United States Patent [19]

Lehmann et al.

[11] Patent Number: 4,798,811

[45] Date of Patent: Jan. 17, 1989

[54] COMBINATION PREPARATION

[75] Inventors: Hans D. Lehmann, Hirschberg/Leutershausen; Rolf Kretzschmar, Gruenstadt; Klaus-Juergen Hahn, Heidelberg, all of Fed. Rep. of Germany

[73] Assignee: BASF Aktiengesellschaft, Fed. Rep. of Germany

[21] Appl. No.: 141,535

[22] Filed: Jan. 7, 1988

Related U.S. Application Data

[63] Continuation-in-part of Ser. No. 917,049, Oct. 9, 1986, abandoned.

[30] Foreign Application Priority Data

Oct. 9, 1986 [DE] Fed. Rep. of Germany ....... 3535950

[51] Int. Cl.$^4$ ............. A61K 31/60; A61K 31/61; A61K /31/605; A61K 31/615
[52] U.S. Cl. .................. 514/159; 514/161; 514/162; 514/163; 514/164
[58] Field of Search ..................... 514/159-164

[56] References Cited

U.S. PATENT DOCUMENTS 4,438,131  3/1984  Ehrmann et al. .............. 549/442

OTHER PUBLICATIONS

Kentera et al. (1979) Respiration 37:192-196.
Susic et al. (1984) Basic Res. Cardio. 79:375-378.
Pharma. Index III/84, Isoptin, Procorum and Colfarit, pp. 1162-1167, 1580-1581 and 705.
Chem. Abst. (1984) 101: 128249j.
Chem Abstr. (1979) 91:102033j.
Arzneim.-Forsch. (Drug Res.) (1973) 23(II):1479.
Lancet (1985) 351.

*Primary Examiner*—Stanley J. Friedman
*Attorney, Agent, or Firm*—Keil & Weinkauf

[57] ABSTRACT

A combination of verapamil, gallopamil or anipamil and acetylsalicylic acid in a weight ratio of from 10:1 to 2:1 being useful in the treatment of circulatory disorders.

6 Claims, No Drawings

COMBINATION PREPARATION

This is a continuation-in-part of application Ser. No. 917,049, filed Oct. 9, 1986, now abandoned.

The present invention relates to a novel combination preparation for the treatment of disorders caused by thrombocyte aggregation.

It is known that cardiac disorders due to an inadequate flow of blood through the tissue (ischemia) can be treated with verapamil, gallopamil and anipamil (cf. list in Pharma Index III/84, Isoptin ® and Procorum ® and European Laid-Open Application No. 64,158). These substances have both a vasodilating action and a cardioprotective and thrombocyte aggregation-inhibiting action. It is also known that, because of its thrombocyte aggregation-inhibiting action, acetylsalicylic acid is used for the prophylaxis of thromboembolic disorders (cf. list in Pharma Index III/84, Colfarit ®).

We have found that the action of verapamil, gallopamil and anipamil can be greatly increased by acetylsalicylic acid.

The present invention relates to a drug which contains, on the one hand, verapamil, gallopamil or anipamil and, on the other hand, acetylsalicylic acid in a weight ratio of from 10:1 to 1:20, preferably from 7:1 to 2:1.

Verapamil is 1,7-bis-(3,4-dimethoxyphenyl)-3-methylaza-7-cyano-8-methylnonane, gallopamil is 1-(3,4-dimethoxyphenyl)-3-methylaza-7-cyano-7-(3,4,5-trimethoxyphenyl)-8-methylnonane and anipamil is 1,7-bis-(3-methoxyphenyl)-3-methylaza-7-cyanononadecane.

The active compounds may be present in the drug in the free form or in the form of their physiologically tolerated salts. Hydrochloric acid, sulfuric acid, phosphoric acid, acetic acid, malonic acid, succinic acid, fumaric acid, maleic acid, citric acid, tartaric acid, lactic acid, amidosulfonic acid and oxalic acid are suitable for salt formation with the compounds 1. Particularly suitable salts of acetylsalicylic acid are the alkali metal and alkaline earth metal salts.

For the novel medicament, it is preferable to use the compounds I in the form of their hydrochlorides and the acetylsalicylic acid in the free form.

The stated mixing ratio is based on the free forms of the substances.

The superior action of the novel combination can be demonstrated by determining the thrombocyte aggregation. The following methods were used:

1. In vitro investigations

Venous blood was taken from four test persons and rendered unclottable by adding citrate, and thrombocyte-rich plasma was then obtained from this blood by centrifuging under 300 g for 10 minutes at 4° C. The addition of adrenalin (final concentration $5 \times 10^{-8}$ mole/liter) and collagen (final concentration $2 \times 10^{-3}$ g/liter) to the thrombocyte-rich plasma caused aggregation, which was measured as the change in extinction using a Born aggregometer MK 3. The maximum change in extinction per second was used as a measure of aggregation. The percentage inhibition of aggregation was determined by comparing the values before and after administration of the substance. Results are shown in Table 1.

TABLE 1

| Substance | Conc. (mg/l) | Aggregation inhibition (%) |
|---|---|---|
| Verapamil | 2 | 8.7 |
| ASA | 1 | 0 |
| Verapamil + ASA | 2 + 1 | 24 |
| Verapamil | 10 | 31 |
| ASA | 1 | 0 |
| Verapamil + ASA | 10 + 1 | 52 |

As can be see from Table 1, an aggregation inhibition of 8.7% and 31% was achieved with Verapamil doses of 2 mg/l and 10 mg/l. Acetylsalicylic acid (ASA) added in a dose of 1.0 mg/l was ineffective. When the two substances were combined in the above-mentioned doses, the activity increased substantially (24 and 52% inhibition).

2. Ex vivo investigations

The candidate compounds were filled into stomach-soluble gelatine capsules and administered orally to five test persons. Venous blood was taken before administration of the substances and four hours after administration. This blood was prepared as under 1 and made to aggregate. The percentage inhibition of aggregation was determined by comparing the values before and after administration of the substance. Results are shown in Table 2.

TABLE 2

| Substance | Dosage (mg) | Aggregation inhibition (%) |
|---|---|---|
| Verapamil | 240 | 33 |
| ASA | 60 | 0 |
| Verapamil + ASA | 240 + 60 | 65 |

Table 2 again shows a substantial increase in aggregation inhibition.

This potentiation effect is surprising and could not be foreseen. On the other hand, the action found has interesting consequences for therapy, since it permits a useful extension of the possible applications of verapamil, gallopamil and anipamil and a reduction in the dose when acetylsalicylic acid is used.

The novel combination is useful for the treatment and prophylaxis of disorders caused by thrombocyte aggregation. These include thromboembolic disorders of the heart, brain and peripheral, arterial vascular systems. Examples of such disorders are myocardial infarction, strokes and obliterative arteriosclerosis.

The novel combination is also useful for the treatment and prophylaxis of disorders caused by the liberation of vasoactive substances from aggregating thrombocytes, e.g. migraines, vasospastic angina and Raynaud's disease.

The combination according to the invention can be administered orally in a conventional manner.

The dose depends on the age, condition and weight of the patient and on the route of administration. As a rule, the daily dose is from about 20 to 500 mg, preferably from 50 to 250 mg, of verapamil, gallopamil or anipamil and from about 10 to 100 mg, preferably from 40 to 80 mg, of acetylsalicylic acid per patient.

The novel combination may be employed in the conventional solid or liquid pharmaceutical forms, for example tablets, film tablets, capsules, powders, granules, coated tablets, pellets, controlled-release pellets or solutions. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retarding agents and/or anti-oxidants (cf. H. Sucker et al: Pharmazeutische Technologie, Thieme-Verlag, Stuttgart, 1978). The formulations thus obtained normally contain from 10 to 99% by weight of the active compound.

EXAMPLE 1

Tablets having the following composition are prepared by pressing on a tabletting machine in a conventional manner:

240 mg of verapamil hydrochloride
50 mg of acetylsalicylic acid
72 mg of corn starch
13 mg of gelatine
35 mg of lactose
25 mg of carboxymethylcellulose
17.5 mg of talc
3.5 mg of magnesium stearate

EXAMPLE 2

Tablet cores having the following composition are prepared in a conventional manner:

50 mg of gallopamil
25 mg of acetylsalicylic acid
100 mg of core material

The core material consists of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating material consists of 5 parts of sucrose, 2 parts of corn starch, 2 parts of calcium carbonate and 1 part of talc.

The cores obtained are then coated with the sugar-coating material having the following composition:

5 parts of sucrose
2 parts of corn starch
2 parts of calcium carbonate
1 part of talc

EXAMPLE 3

For the preparation of film tablets, the tablet cores prepared as described in Example 2 are coated with a film coating having the following composition:

| Tylose | 0.7% | Corn starch | 2.0% |
| ® Kollidon 25 (PVP) | 0.4% | Calcium carbonate | 3.5% |
| Sucrose | 70.0% | Gum arabic | 2.5% |
| Finely divided silica | 1.4% | Titanium dioxide + | |
| Talc | 11.0% | Colorants | 8.5% |

EXAMPLE 4

Controlled-release pellets which can be introduced into hard gelatin capsules are prepared, each component being pelletized separately. The controlled-release pellets are then introduced into the capsules either as a mixture or in succession, each pelletized component being present in the capsule in a 1:1 ratio based on weight.

Composition of the pellets per dose:
Controlled-release pellets, compound I:
50 mg of gallopamil hydrochloride
60 mg of cellulose powder
5 mg of corn starch
10 mg of talc
35 mg of ethylcellulose
Controlled-release pellets, compound II:
20 mg of acetylsalicylic acid
20 mg of cellulose powder 10 mg of corn starch
10 mg of ethylcellulose

EXAMPLE 5

Pellets which can be introduced into hard gelatine capsules and have the following composition are prepared:

200 mg of verapamil
20 mg of acetylsalicylic acid
80 mg of cellulose powder
30 mg of corn starch
5 mg of ®Kollidon 30 (PVP)
20 mg of ®Eudragit S (polymer of methacrylic acid and methacrylates)
15 mg of talc

We claim:

1. A pharmaceutical composition for the treatment of circulatory disorders comprising a member selected from the group consisting of verapamil, gallopamil, anipamil, physiologically tolerated salts thereof and mixtures thereof and acetylsalicylic acid in the weight ratio of from 10:1 to 2:1.

2. The composition of claim 1 comprising verapamil or its hydrochloride and acetylsalicylic acid.

3. The composition of claim 2 wherein the weight ratio is 7:1 to 2:1.

4. The composition of claim 1 wherein the weight ratio is 7:1 to 2:1.

5. A method of treating and preventing disorders caused by thrombocyte aggregation comprising: administering to a patient in need thereof an effective amount of the composition of claim 1.

6. A method of treating and preventing disorders caused by thrombocyte aggregation comprising: administering to a patient in need thereof an effective amount of the composition of claim 2.

* * * * *